(12) United States Patent
Lee et al.

(10) Patent No.: US 10,290,785 B2
(45) Date of Patent: May 14, 2019

(54) LAMINATING STRUCTURE OF ELECTRONIC DEVICE USING TRANSFERRING ELEMENT, TRANSFERRING APPARATUS FOR FABRICATING THE ELECTRONIC DEVICE AND METHOD FOR FABRICATING THE ELECTRONIC DEVICE

(71) Applicant: CENTER FOR INTEGRATED SMART SENSORS FOUNDATION, Daejeon (KR)

(72) Inventors: Keon Jae Lee, Daejeon (KR); Han Eol Lee, Daejeon (KR); Do Hyun Kim, Daejeon (KR); Jung Ho Shin, Daejeon (KR); Seong Kwang Hong, Daejeon (KR)

(73) Assignee: CENTER FOR INTEGRATED SMART SENSORS FOUNDATION, Daejeon (KR)

( * ) Notice: Subject to any disclaimer, the term of this patent is extended or adjusted under 35 U.S.C. 154(b) by 0 days.

(21) Appl. No.: 15/724,016

(22) Filed: Oct. 3, 2017

(65) Prior Publication Data

US 2019/0103532 A1    Apr. 4, 2019

(51) Int. Cl.
*H01L 33/62*    (2010.01)
*H01L 23/00*    (2006.01)
(Continued)

(52) U.S. Cl.
CPC ........... *H01L 33/62* (2013.01); *A61B 5/0084* (2013.01); *A61B 5/6868* (2013.01); *A61N 5/0601* (2013.01); *H01L 23/5387* (2013.01); *H01L 24/75* (2013.01); *H01L 24/83* (2013.01); *A61N 2005/0612* (2013.01);
(Continued)

(58) Field of Classification Search
CPC ..... H01L 33/62; H01L 23/5387; H01L 24/75; H01L 24/83; H01L 2224/753; H01L 2224/75651; H01L 2224/75744; H01L 2224/75753; H01L 2224/83005; H01L 2224/8316; H01L 2224/83203; H01L 2224/83851; H01L 2924/1579; H01L 2933/0066; A61B 5/0084; A61B 5/6868; A61N 5/0601
See application file for complete search history.

(56) References Cited

U.S. PATENT DOCUMENTS 7,622,367 B1*  11/2009  Nuzzo ............... B82Y 10/00
                                            438/472
2010/0317132 A1* 12/2010 Rogers ............. H01L 25/0753
                                            438/27

FOREIGN PATENT DOCUMENTS

KR    10-0700824    3/2007
KR    10-1362516    2/2014

* cited by examiner

*Primary Examiner* — Matthew C Landau
*Assistant Examiner* — Dmitriy Yemelyanov

(57) ABSTRACT

A laminating structure of an electronic device using a transferring element according to the present disclosure includes a target substrate, a bottom electrode formed on the target substrate, an electronic device which is bonded to the bottom electrode, a top contact formed on the electronic device, a transferring element which is placed between the bottom electrode and the electronic device on the target substrate, and a top electrode connected to the electronic device, wherein the transferring element attached to the carrier substrate comes into contact with the electronic device, and is then transferred onto the target substrate.

12 Claims, 16 Drawing Sheets

Final protective film formation

(51) Int. Cl.
*A61B 5/00* (2006.01)
*A61N 5/06* (2006.01)
*H01L 23/538* (2006.01)

(52) U.S. Cl.
CPC .......................... *A61N 2005/0651* (2013.01); *H01L 2224/753* (2013.01); *H01L 2224/75651* (2013.01); *H01L 2224/75744* (2013.01); *H01L 2224/75753* (2013.01); *H01L 2224/83005* (2013.01); *H01L 2224/8316* (2013.01); *H01L 2224/83203* (2013.01); *H01L 2224/83851* (2013.01); *H01L 2924/12041* (2013.01); *H01L 2924/1579* (2013.01); *H01L 2933/0066* (2013.01)

Formation of multilayer thin film which makes up LED on mother wafer

LED cell isolation and top electrode deposition/formation

LED chip attachment to temporary carrier wafer

Top electrode fabrication

Final protective film formation

LAMINATING STRUCTURE OF ELECTRONIC DEVICE USING TRANSFERRING ELEMENT, TRANSFERRING APPARATUS FOR FABRICATING THE ELECTRONIC DEVICE AND METHOD FOR FABRICATING THE ELECTRONIC DEVICE

BACKGROUND OF THE INVENTION

Field of the Invention

The present disclosure relates to a laminating structure of an electronic device using a transferring element, a transferring apparatus for fabricating the electronic device and a method for fabricating the electronic device using the transferring element, and more particularly, to technology that forms a light emitting diode (LED) inorganic multilayer or layers that make up an inorganic LED on a mother wafer, enables isolation of each chip, moves and attaches the inorganic LED from the mother wafer to a carrier substrate, and transfers the isolated LED chips attached to the carrier substrate onto a flexible target substrate with electrodes by the medium of a transferring element, thereby realizing the flexible LED device in the form of an individual chip or an array.

Furthermore, the present disclosure relates to a transferring apparatus that enables connection between a target substrate and a carrier substrate aligned vertically through a transferring element, wherein the target substrate with electrodes has flexible properties, and the transferring element enables electrical connection and adhesion between the carrier substrate and the target substrate, and more particularly, to technology that performs bonding under high pressure and temperature on a carrier substrate and a target substrate aligned vertically with a transferring element interposed between the carrier substrate and the target substrate, wherein as an embodiment of an electronic device having undergone isolation of each chip on a mother wafer, an LED inorganic multilayer is temporarily attached to the carrier substrate, the target substrate has electrodes, and the transferring element enables electrical connection and adhesion.

Description of the Related Art

A flexible electronic device refers to an electronic device that bends or curves when subjected to a predetermined force. This flexible device needs to be flexible per se, and a substrate below the device and a coating layer that covers the device also needs to possess a predetermined level of flexibility. A general very large scale integrated circuit (VLSI) is fabricated by combining a plurality of lighter and smaller electronic devices such as transistors and capacitors into a silicon substrate, and it cannot be used over a wide range of applications due to the limitation of rigid properties inherent in the silicon substrate. To overcome the conventional problem, separating a high-performance electronic device from a rigid substrate and accurately transferring it onto a desired substrate becomes more and more important, and to impart flexibility to a large-scale electronic device such as display or a large scale integrated circuit (LSI), yield and stability of a transfer method is the key. That is, to improve a stable laminating structure of an electronic device in keeping up with the trend toward larger scale electronic devices, a flexible device should be fabricated first through iterative transferring processes.

Recently, many studies are being made on the fabrication of a device such as an inorganic light emitting diode (LED) on a flexible substrate, and a conventional method for fabricating a flexible device generally includes fabricating a device on a substrate and separating the device by a wet etching method, but in this case, an alignment problem in the device during wet etching and a procedural problem occur.

For a conventional process for fabricating a flexible device in relation to a vertical LED, reference is made to Patent No. 10-1362516 published on Feb. 14, 2014, wherein connection between circuitry and an inorganic device formed on a flexible substrate requires a transfer process and adhesion of anisotropic conductive film using heat and pressure or adhesion between metals. The method has a limitation in reducing the thickness of the flexible substrate due to the anisotropic conductive film, has lower yield with the smaller size of the LED, and has a spatial error that may occur in connecting the circuitry and the LED formed on the flexible substrate.

In the fabrication of a micro LED, a process for stably transferring onto a flexible substrate is important, and to improve a laminating structure of the micro LED in keeping up with the trend toward larger scale micro LEDs, there is a need for an approach to separate a high-performance electronic device from a rigid substrate and accurately transfer it with an aim of improving the yield and stability.

For the yield and stability of the transfer process, there is an urgent need for development of an apparatus that efficiently performs a transfer process on a target flexible substrate and a carrier substrate, to which a flexible electronic device is temporarily attached, in alignment by the medium of a predefined transferring element.

For a conventional laser thermal transfer apparatus and a method for preparing an organic LED using the same, reference is made to Patent No. 10-0700824 published on Mar. 27, 2007, wherein an acceptor substrate and a donor film are placed on a substrate stage in a manner allowing upward and downward movement, and laser irradiated through a laser resonator is illuminated over the entire area of the donor film.

Meanwhile, a process for integrating the flexible electronic device into the flexible substrate in the vertical arrangement of the flexible substrate, the carrier substrate and the transferring element interposed between the substrates requires high precision.

SUMMARY OF THE INVENTION

The present disclosure is designed to solve the conventional problems, and therefore the present disclosure is directed to providing a method that forms a light emitting diode (LED) inorganic multilayer or layers that make up an inorganic LED on a mother wafer, enables isolation of each chip, attaches the isolated chips to a temporarily used carrier substrate, removes the mother wafer, transfers the isolated LED chips onto a flexible target substrate with electrodes by the medium of a transferring element, and enables interconnection, thereby realizing the flexible LED device in the form of an individual chip or an array.

The present disclosure is further directed to providing an apparatus that performs bonding under high pressure and temperature on a carrier substrate to which a flexible electronic device having undergone isolation of each chip on a mother wafer is temporarily attached and a target substrate with electrodes in vertical alignment using a special microscope having vertical alignment optical function, with a transferring element interposed between the carrier substrate and the target substrate to enable electrical connection and adhesion.

To achieve the object, a laminating structure of an electronic device using a transferring element according to an aspect of the present disclosure includes a target substrate, a bottom electrode formed on the target substrate, an electronic device which is bonded to the bottom electrode, a top contact formed on the electronic device, a transferring element which is placed between the bottom electrode and the electronic device on the target substrate, and a top electrode connected to the electronic device, wherein the transferring element attached to the carrier substrate comes into contact with the electronic device, and is then transferred onto the target substrate.

The electronic device is a micro LED device or a large scale integrated circuit (LSI).

The target substrate is a flexible plastic substrate or a polymer substrate.

The electronic device has a structure in which the electronic device temporarily attached to the carrier substrate is bonded to the transferring element which is deformed by an external force, and is transferred onto the target substrate.

The external force is any one of a group including heat, pressure, ultrasonic wave, mechanical force and van der Waals force, and the transferring element is any one of a conductive adhesive material group including Anisotropic Conductive Film (ACF), Self Organized Conductive Film (SOCF), Anisotropic Conductive Adhesive (ACA) and solder ball.

To achieve the object, a method for fabricating an electronic device using a transferring element according to another aspect of the present disclosure includes preparing a mother wafer, forming an inorganic material-based multilayer thin film layer which makes up an electronic device on the mother wafer, individually isolating the electronic device formed on the multilayer thin film layer, attaching a carrier substrate to the electronic device, removing the mother wafer, aligning positions of a bottom electrode formed on a target substrate and the electronic device on the carrier substrate, placing a transferring element between the target substrate and the electronic device and performing bonding, and removing the carrier substrate.

The electronic device is a micro LED device or a large scale integrated circuit (LSI).

The target substrate is a flexible plastic substrate or a polymer substrate.

The individually isolating of the electronic device includes isolating the electronic device for each chip through masking and etching.

The attaching of the carrier substrate formed on the multilayer thin film layer to the electronic device includes forming a primary protective layer on a side surface of the electronic device to protect the electronic device.

The primary protective layer is an oxide layer or a polymer layer.

The method further includes, after the removing of the carrier substrate, forming a top electrode connected to the electronic device.

The method further includes, before the forming of the top electrode, forming a secondary protective layer on an empty space around the electronic device to prevent a short between the bottom electrode and the top electrode.

The secondary protective layer is an oxide layer or a polymer layer.

The carrier substrate is any one of a group including PDMS, a thermal release tape, a UV release tape and a water soluble tape.

At the bonding, when the transferring element is selectively applied to the target substrate and the electronic device temporarily attached to the carrier substrate is bonded, bonding is only performed on the electronic device placed on an area of the target substrate to which the transferring element is applied.

At the bonding, when only part of the electronic device on the carrier substrate is applied to the transferring element, the part of the electronic device is selectively transferred.

At the bonding, when the transferring element is entirely applied to the target substrate and the entire electronic device on the carrier substrate is bonded, simultaneous transfer and interconnection of the entire electronic device is achieved.

The removing of the mother wafer is performed through etching or laser lift off process.

The transferring element is any one of a group including anisotropic conductive film, Non Conductive Film (NCF), Self Organized Conductive Film (SOCF), Anisotropic Conductive Adhesive (ACA) and solder ball.

The bonding uses any one of bonding means including ultrasonic wave, mechanical force, van der Waals force, and heat and pressure.

The masking is any one of a group including metal masking, masking using PR, masking using polymer, and soft masking.

To achieve the object, a transfer and packaging apparatus according to still another aspect of the present disclosure includes a hollow process chamber, a base plate placed in the process chamber, a motion module placed on the base plate, a stage module placed moveably parallel to the ground by the motion module, an optical controller placed moveably above the stage module apart from the stage module, and a carrier substrate suction unit placed above the stage module such that the carrier substrate suction unit can be moved up and down, wherein transfer is performed on a target substrate mounted on any one of the multiple stages which constitute the stage module and a carrier substrate mounted on the carrier substrate suction unit using any one of protocols including stamping, ACF, SOCF, and UV methods.

To achieve the object, a transfer method according to further another aspect of the present disclosure includes preparing a mother wafer on one of multiple stages which constitute a stage module, forming an inorganic material-based multilayer thin film layer which makes up an electronic device on the mother wafer, individually isolating the electronic device formed on the multilayer thin film layer, connecting a carrier substrate mounted on a carrier substrate suction unit to the mother wafer to thereby connect the electronic device to the carrier substrate, removing the mother wafer, placing a target substrate on another stage of the multiple stages constituting the stage module, aligning the carrier substrate suction unit with the stage on which the target substrate is mounted, placing a transferring element between the target substrate and the carrier substrate through a process for moving down the carrier substrate suction unit to apply an external force and performing bonding, and removing the carrier substrate.

According to the present disclosure described as above, a LED inorganic multilayer that makes up an inorganic LED is formed on a mother wafer, followed by isolation of each chip, and the isolated LED chips are transferred onto a flexible target substrate with electrodes by the medium of a transferring element and interconnection is established, so that the flexible LED device is realized in the form of an individual chip or an array, and anisotropic conductive film (ACF) is, for example, used as the transferring element during transfer of the LED and plays a role in not only providing an adhesive strength for transfer but also establishing electrical interconnection, thereby allowing a simple and stable process.

The present disclosure allows selective transfer for each area because only an area to which the transferring element is applied has an adhesive strength, making it possible to transfer the LED chip from the temporary substrate or carrier substrate to the flexible target substrate, which enables individual transfer of a RGB LED chip, and formation of RGB pixel and flexible display.

The present disclosure enables the transfer of all the chips with the application of the transferring element over the entire area, allowing applications in lighting or mono color display. Here, the use of quantum dots (QDs) as a color filter can achieve formation of RGB pixel and flexible display.

A final structure of the flexible micro inorganic LED device through the fabrication method according to the present disclosure is flexible vertical micro inorganic LEDs, and the device is so thin and flexible that it can be implanted into a narrow space between brain and skull.

It realizes flexible displays using the micro-sized inorganic LED, and covers applications for inorganic LED lighting, wearable devices and bio-integrated devices.

The present disclosure uses anisotropic conductive film (ACF) for transfer of the LED, which enables simultaneous transfer and interconnection, leading to a stable process, and accordingly, it allows mass production and is suitable for commercialization.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
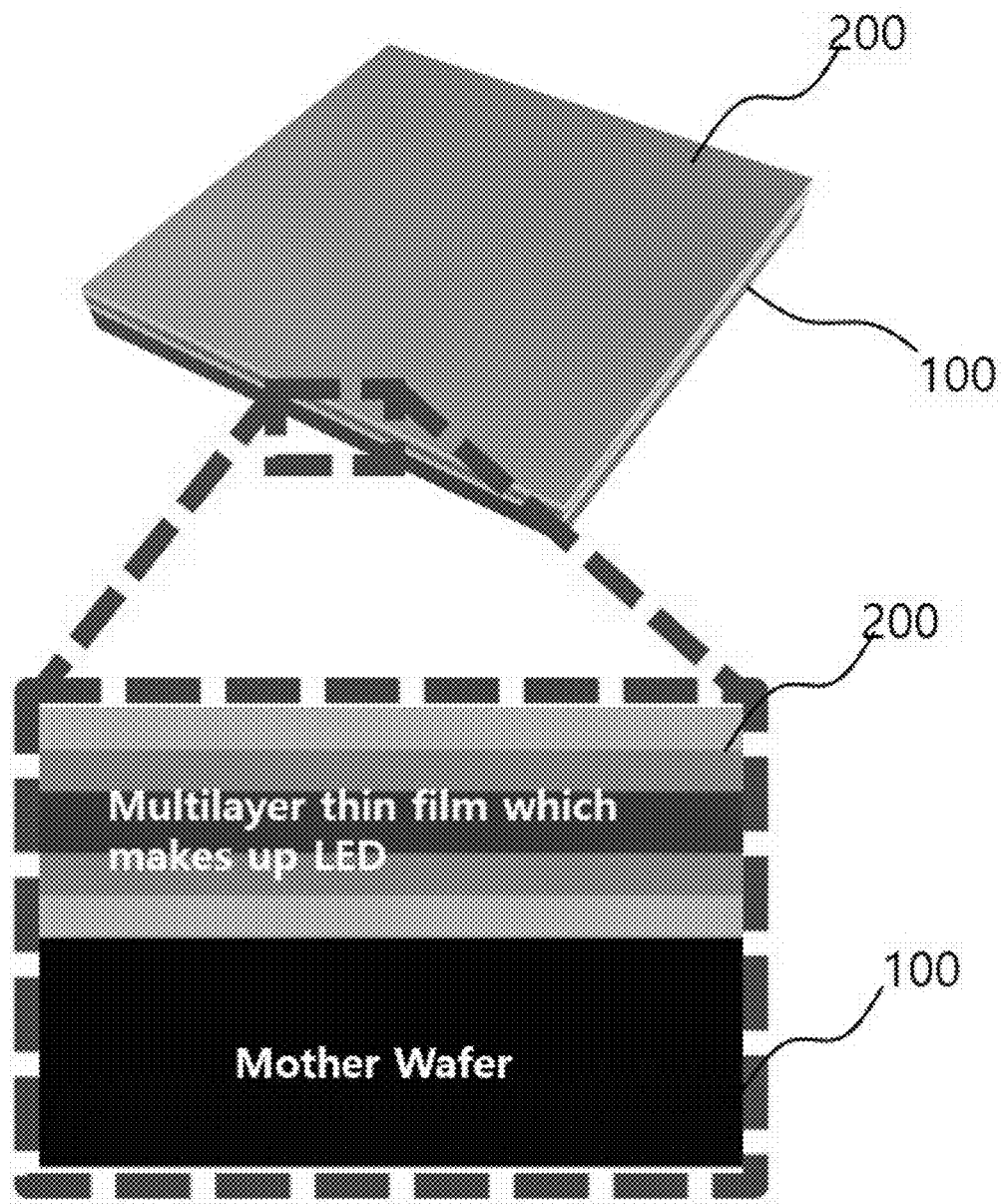
FIGS. 1 to 13 are diagrams sequentially illustrating a method for fabricating a flexible micro inorganic light emitting diode (LED) device according to an embodiment of the present disclosure.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

The term "flexible" as used herein refer to all properties whereby a substrate such as a plastic substrate can be bent at a predetermined angle or folded, compared to a silicon substrate having rigid properties.

The present disclosure realizes a flexible electronic device in the form of a chip or an array by transferring an electronic device attached to a temporarily used carrier substrate onto a flexible target substrate with electrodes by the medium of a transferring element and enabling interconnection. The electronic device includes a micro inorganic light emitting diode (LED) device and a large scale integrated circuit (LSI). Meanwhile, the target substrate may be a flexible plastic substrate or a polymer substrate.

Hereinafter, a method for fabricating a laminating structure of an electronic device using a transferring element according to the present disclosure is described in detail by use of the drawings.

Generally, an electronic device or a micro LED device refers to an ultra-small LED of 10 to 100 micrometers (μm)

in size, and when compared to conventional LED chips, its length is about 1/10 and its area is about 1/100.

The micro LED supports a fast response speed, low power and high brightness as compared to conventional LEDs, and its advantage is that it bends rather than shattering in display applications. Accordingly, it can be applied to smart watches, smart fabrics and head-mounted displays (HMDs) requiring ultralight weight.

Hereinafter, a method for forming a laminating structure of an electronic device using a transferring element according to an embodiment of the present disclosure is described sequentially with reference to FIGS. 1 to 10.

Referring to FIG. 1, an inorganic material-based multilayer thin film 200 that makes up a LED is deposited and formed on a mother wafer 100.

The multilayer thin film 200 stacked on the mother wafer 100 differs depending on the type of the LED, and accordingly, the type of the mother wafer differs as well.

For example, the mother wafer 100 includes GaAs wafer (GaP_yellow and green light, AlGaAs_red and IR light, AlGaInP_yellow, orange and red light) and sapphire wafer (GaN_blue light, InGaN_blue, green, and UV light), and many wafers including them can be applied to the process.

Figure 2:
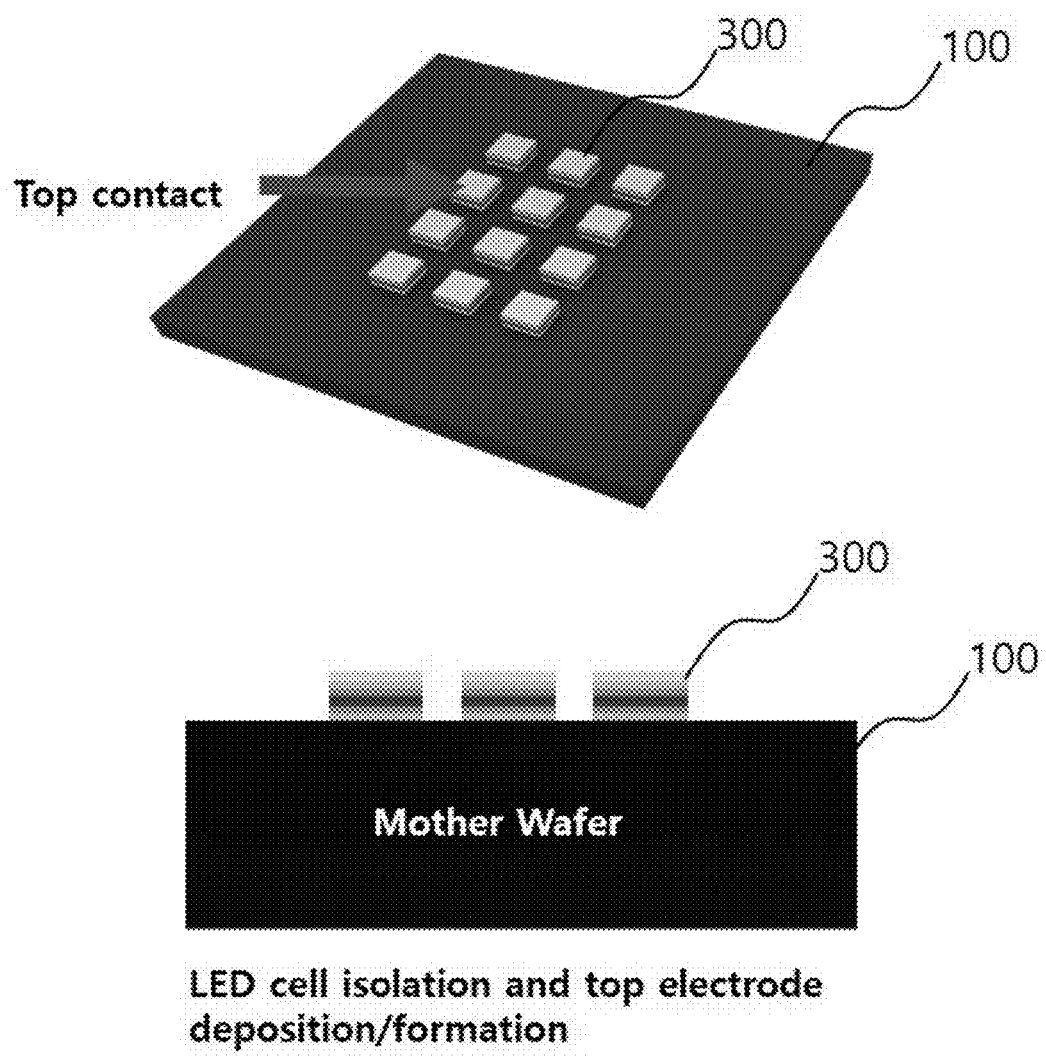

Referring to FIG. 2, the micro LED device 300 undergoes chip isolation through masking and etching sequentially performed on the multilayer thin film 200, and top contact is formed on the isolated LED chip by deposition.

The masking may be any one of a group including metal masking, masking using PR, masking using polymer and soft masking, but is not limited thereto, and other masking techniques enabling selective isolation of the micro LED device may be applied.

Figure 3:
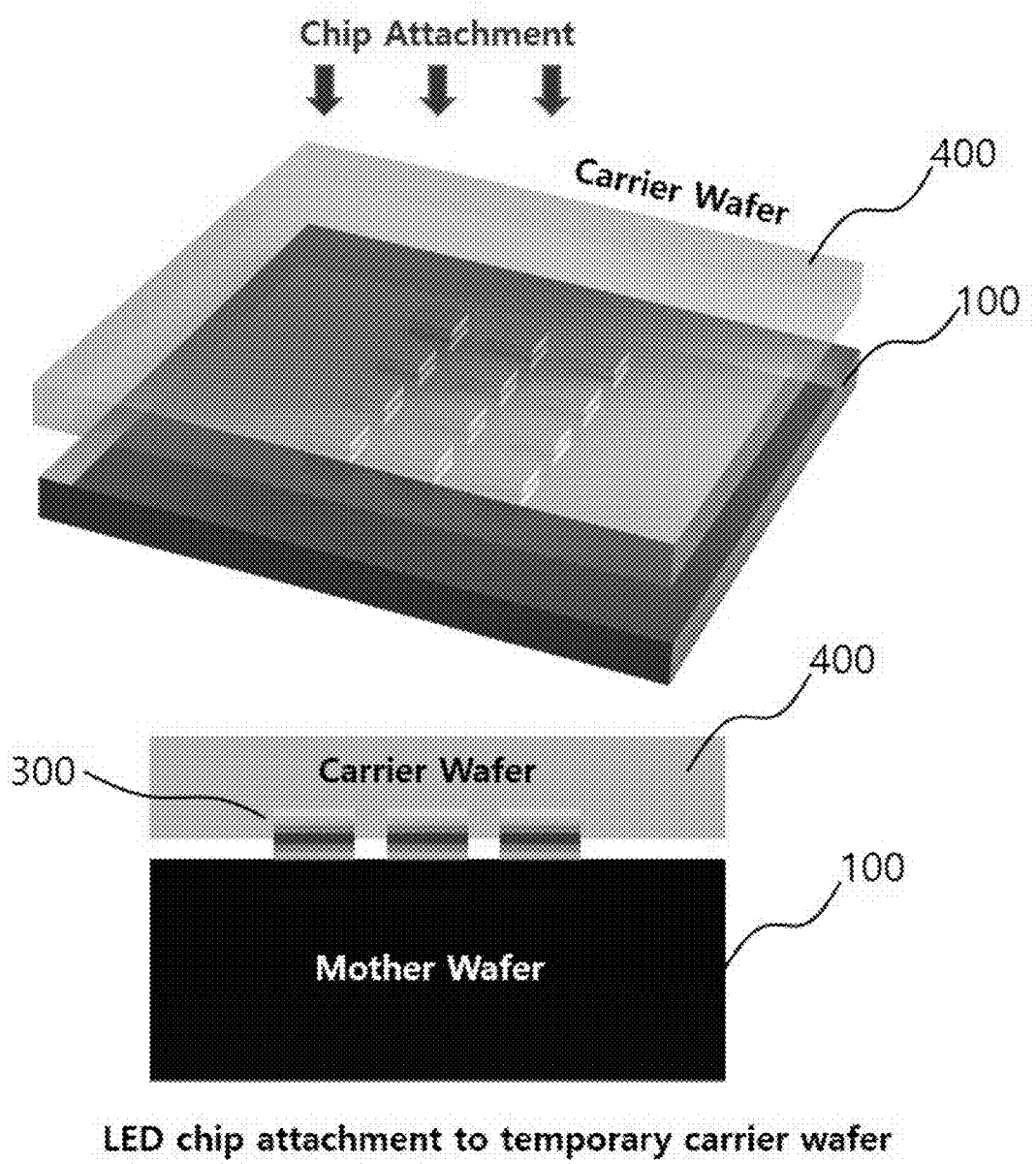

Referring to FIG. 3, a temporary substrate or carrier substrate 400 is attached to the top of the LED chip 300. During attaching, the top contact of the LED chip 300 is inserted into and attached to the lower surface of the carrier substrate 400.

The carrier substrate 400 that can be used in the process includes PDMS, a thermal release tape, and a UV release tape, but is not limited thereto, and many different types of substrates allowing attachment of the LED chip may be applied.

Figure 4:
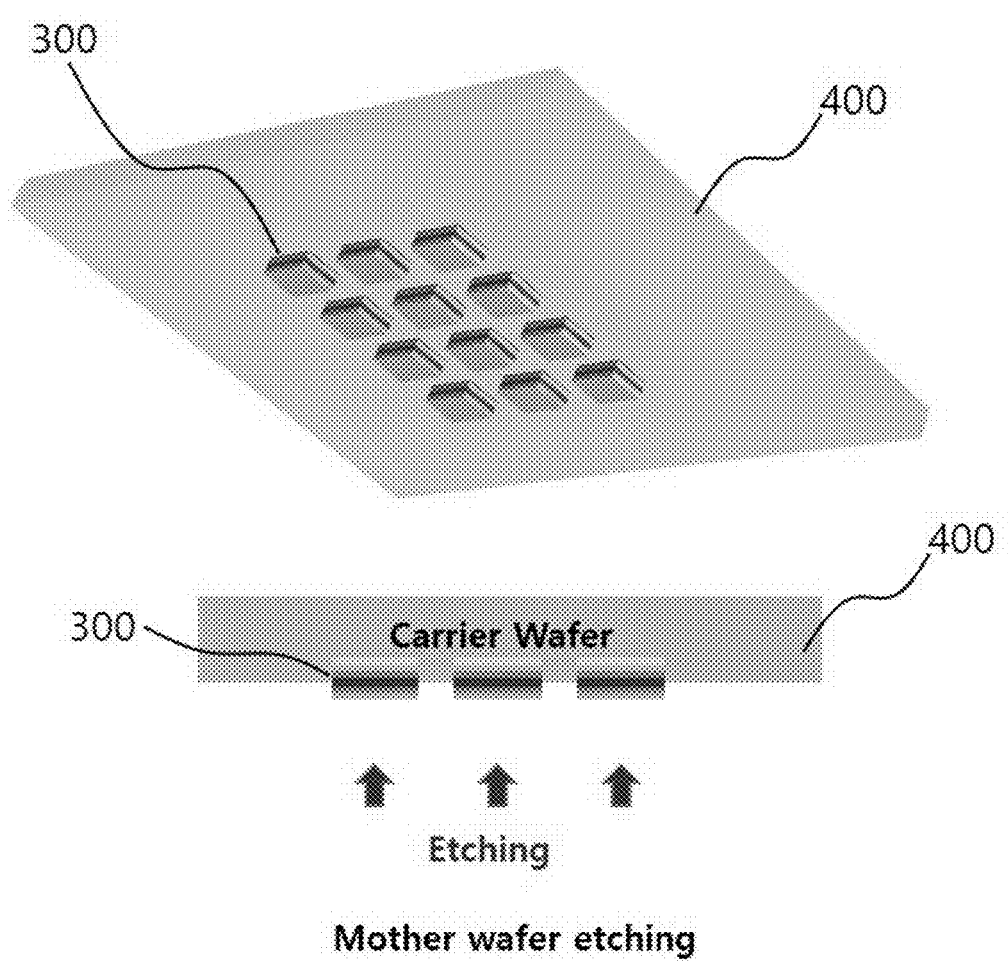

Referring to FIG. 4, the mother wafer 100 is removed through a mechanical or chemical method, and through this, finally, the micro LED chips are attached to the carrier substrate 400. Specifically, removal of the mother wafer 100 is performed through etching or laser lift off process.

Meanwhile, before removing the mother wafer 100, a primary protective layer is formed on the side surface of the LED to protect the LED. That is, an appropriate primary protective layer such as an oxide layer and a polymer layer may be formed on the side surface of the LED to protect the LED during the removal process of the mother wafer 100.

Figure 5:
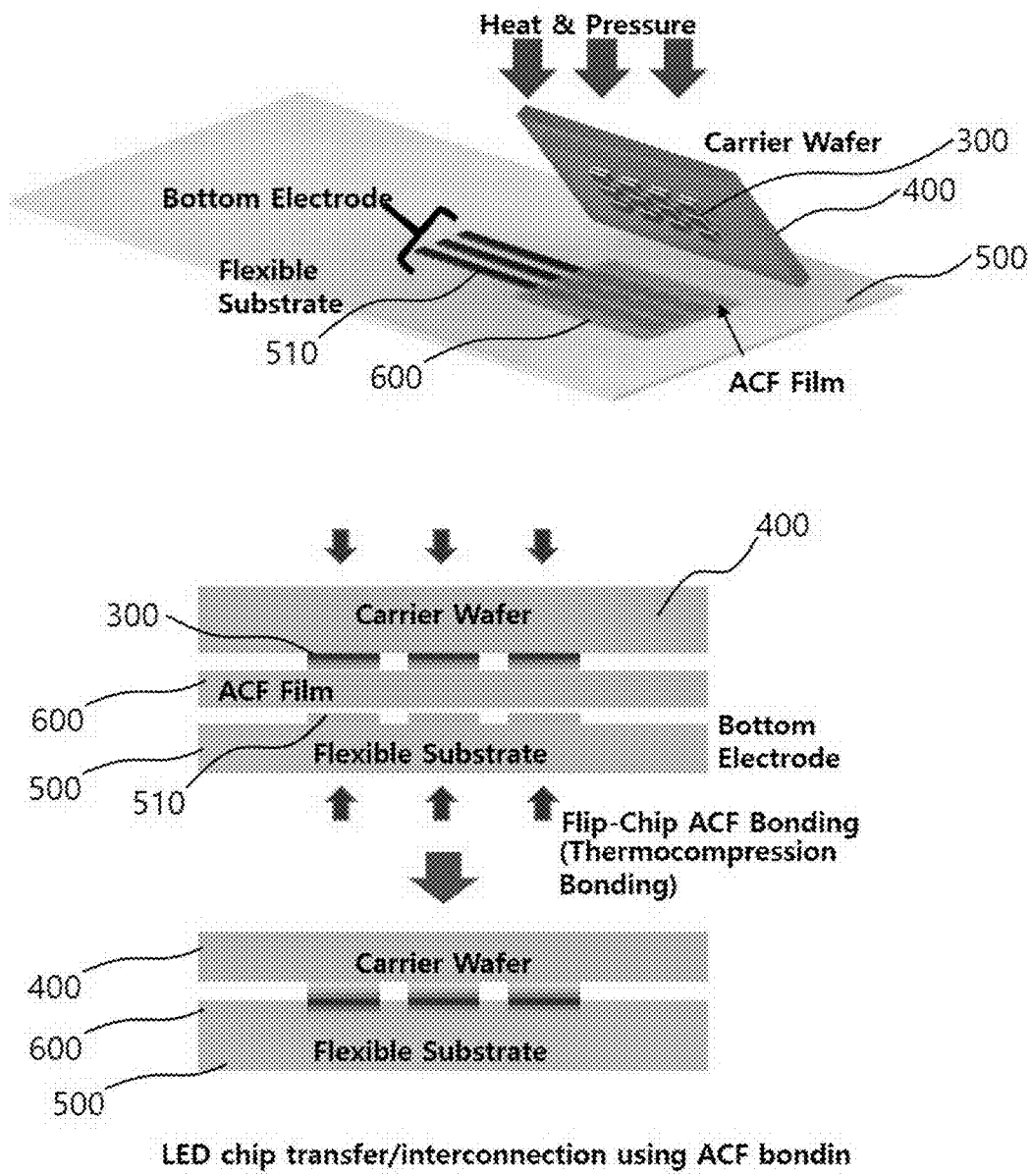

Referring to FIG. 5, the positions of bottom electrode 510 formed on a flexible substrate 500 and the LED chip 300 on the carrier substrate 400 are aligned, and a transferring element 600 is interposed between the flexible substrate 500 and the carrier substrate 400. In this state, bonding is performed on the transferring element 600 using any one of bonding techniques including ultrasonic wave, mechanical force, van der Waals force, and heat and pressure.

The transferring element 600 may exploit various technologies such as anisotropic conductive film (ACF), Non Conductive Film (NCF), Self Organized Conductive Film (SOCF), Anisotropic Conductive Adhesive (ACA), and solder ball. Meanwhile, the transferring element is not limited thereto, and many different types of substrates allowing attachment of the LED chip may be applied.

For the transferring element 600, anisotropic conductive film (ACF) is described for illustration.

The anisotropic conductive film (ACF) applied to the present disclosure achieves thermoscompression bonding when subjected to heat and pressure, and after bonding, it provides secure adhesion and enables electrical interconnection, resulting in a simple and stable process. In addition, its final structure is simple, and the resistance to bending is strong.

Meanwhile, the process for connecting the transferring element 600 between the flexible substrate 500 and the carrier substrate 400 is not limited to a bonding process, and many different techniques or processes enabling connection or joint between multiple substrates may be applied.

The present disclosure may perform a variety of processes in the process for bonding the flexible substrate 500 and the inorganic LED device 300 on the carrier substrate 400 through the transferring element 600.

Figure 6:
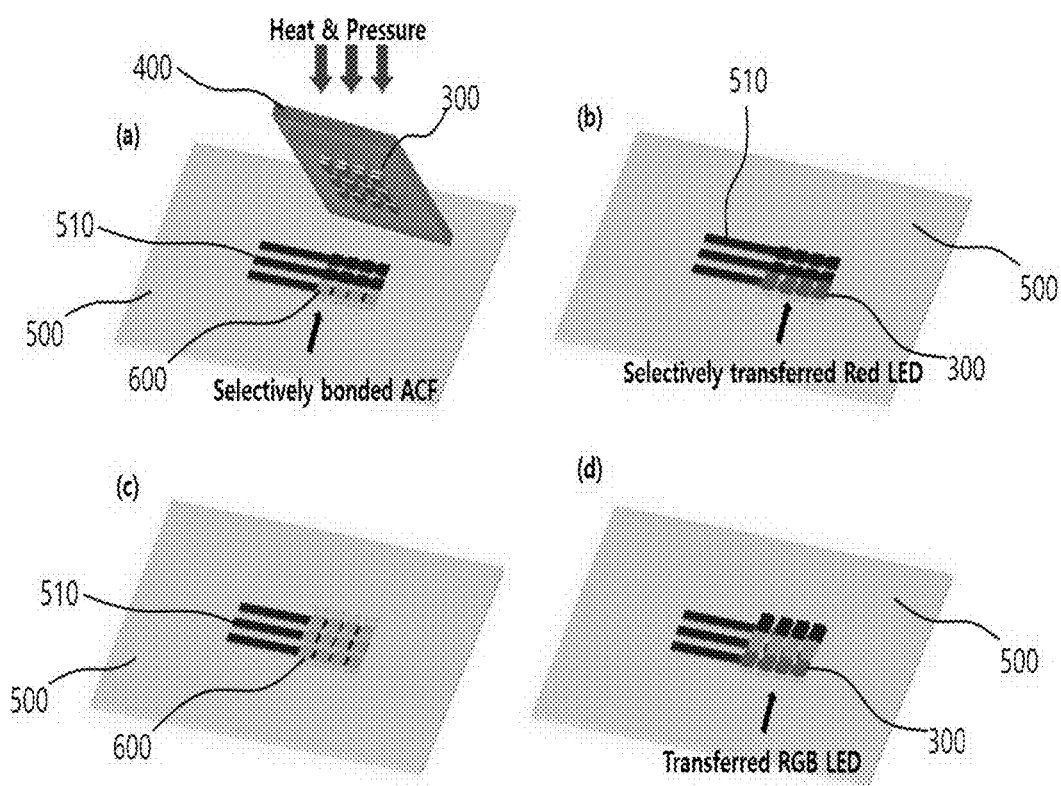

As an embodiment, referring to FIG. 6, when the inorganic LED device 300 temporarily attached to the carrier substrate 400 is bonded to the transferring element 600 selectively applied to the flexible substrate 500, bonding is only performed on the inorganic LED 300 placed on an area of the flexible substrate 500 to which the transferring element 600 is practically applied. That is, because only an area of the flexible substrate to which the transferring element is applied has an adhesive strength, for example, when the transferring element or anisotropic conductive film is selectively applied to a desired position and the inorganic LED of the carrier substrate is bonded, transfer and interconnection takes place at only the inorganic LED on the applied anisotropic conductive film.

Figure 7:
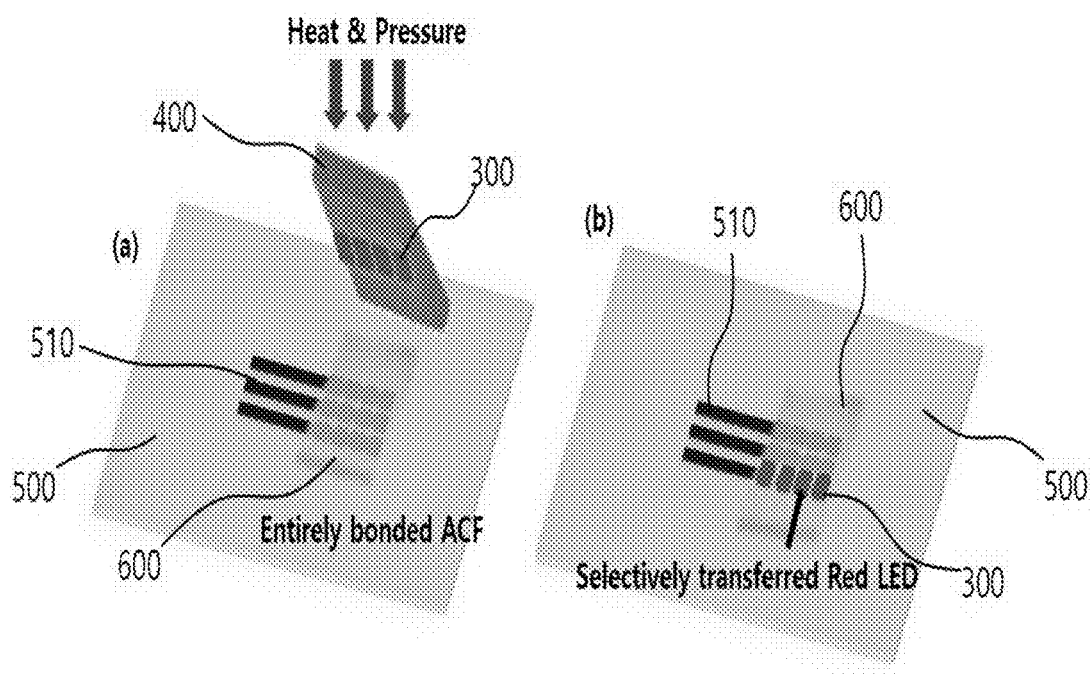

As another embodiment, referring to FIG. 7, the transferring element 600 is applied over the entire flexible substrate 500, and only part of the inorganic LED device 300 of the carrier substrate 400 is selectively bonded. That is, only part of the LED device on the carrier substrate is applied to the transferring element, and the part of the LED device is thus selectively transferred.

Figure 8:
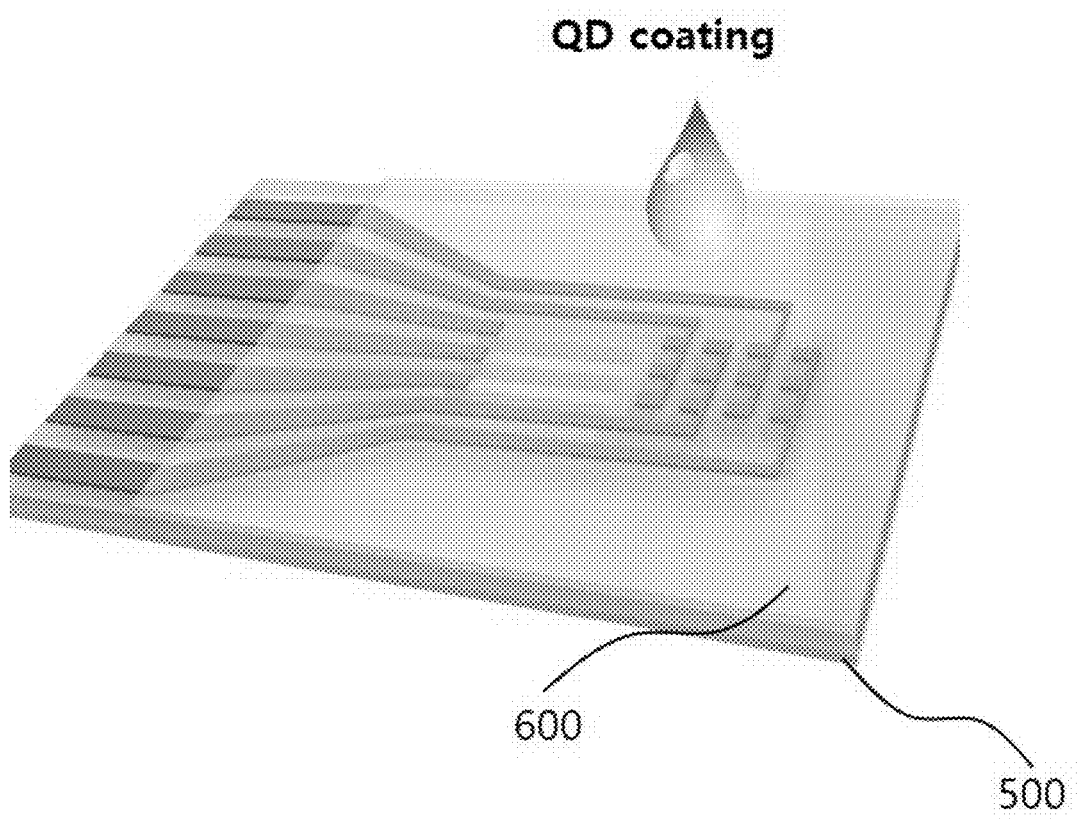

As still another embodiment, referring to FIG. 8, the transferring element 600 is applied over the entire flexible substrate 500, and the entire inorganic LED device 300 of the carrier substrate 400 is bonded at one time. That is, when the transferring element or anisotropic conductive film is applied over the entire flexible substrate and the entire micro LED on the carrier substrate is bonded, simultaneous transfer and interconnection of the entire chip is accomplished. Subsequently, after top electrode is formed, RGB pixel is formed using quantum dots (QDs) as a color filter, and a flexible display is formed.

As described above, it is possible to transfer only some of the LED chips 300 on the carrier substrate 400 based on an area to which the transferring element 600 is applied. That is, because only an area to which the transferring element is applied has an adhesive strength, transfer of the LED chip from the temporary carrier substrate to the flexible substrate takes place, thereby allowing selective transfer for each area.

This enables the transfer of the LED chip in a desired pattern, and formation of RGB pixel and flexible display.

Meanwhile, when the transferring element is applied over the entire area of the LED chips on the carrier substrate, transfer of the entire chip can be accomplished, allowing applications in lighting or mono color display. Here, the use of quantum dots (QDs) as a color filter can achieve formation of RGB pixel and flexible display.

Figure 9:
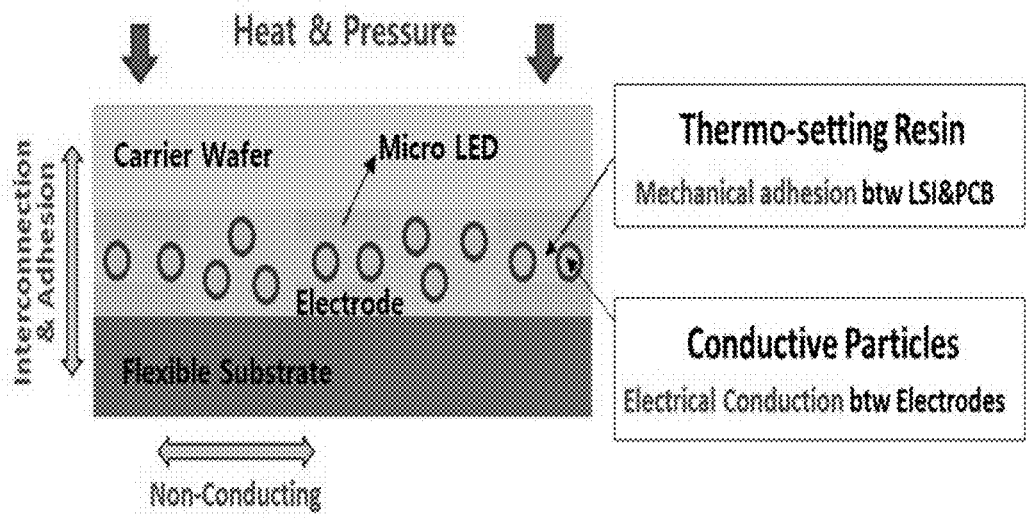

Referring to FIG. 9, flip-chip bonding packaging technology is suitable for flexible packaging because of a simple final shape with a flat structure.

Flip-chip bonding is a type of packaging method including placing a chip or device face-down on a substrate and establishing an electrical connection. Particularly, packaging using ACF maintains electrical connection well under extremely mechanical bending and flexing situation.

Flip-chip bonding involves placing the LED device and the flexible wafer in face-to-face configuration and applying heat and pressure, or ultrasonic wave and pressure, and electrodes facing in the vertical direction exhibit conducting properties and electrodes facing in the horizontal direction exhibit insulation properties. The curing of thermo-setting resin ensures strong mechanical adhesion between LSI and PCB.

Figure 10:
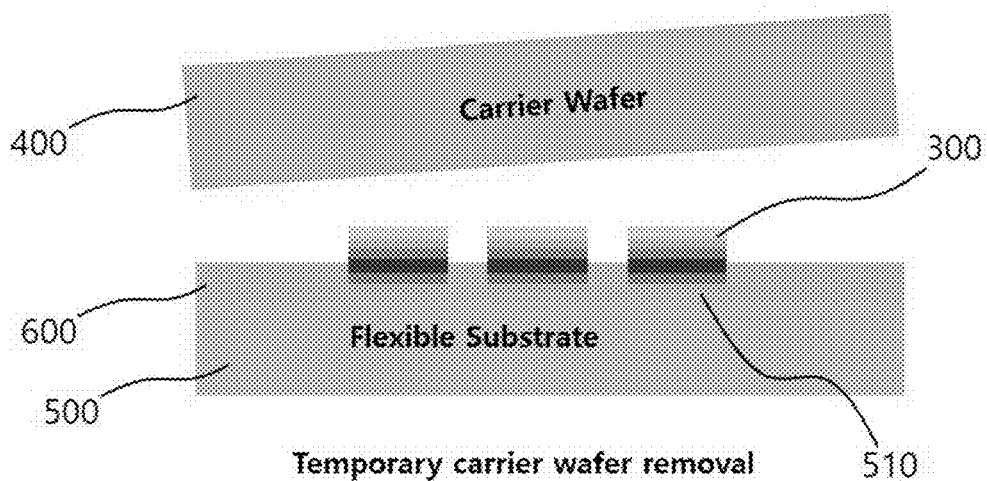

Referring to FIG. 10, a process for removing the carrier substrate 400 is shown.

The process for removing the carrier substrate 400 changes a removal method depending on the carrier substrate used. For example, the carrier substrate 400 may include three substrates of PDMS, a thermal release tape and a UV release tape, and these three carrier substrates can be each removed in a sequential order through the peel speed, the application of heat, and the application of UV.

Figure 11:
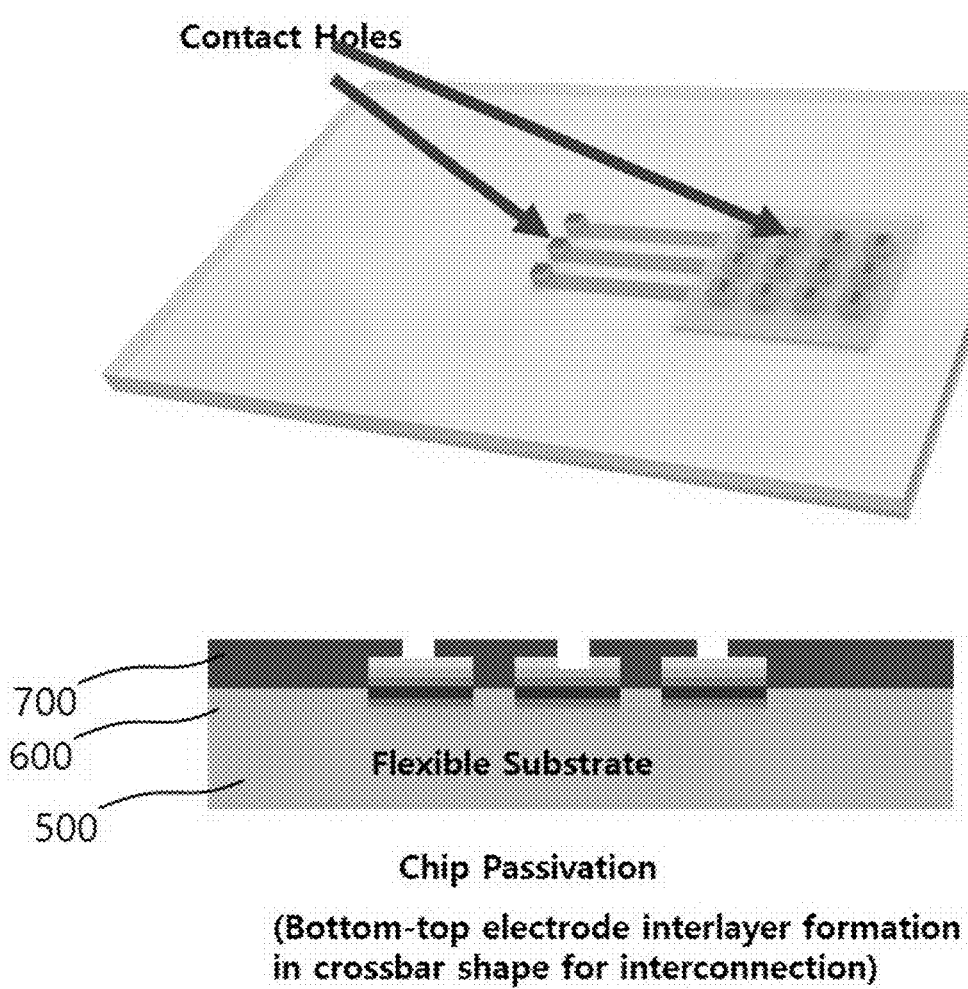

Subsequently, referring to FIG. 11, before connecting the top electrode 800 to the top contact formed on the LED chip 300, a secondary protective layer 700 is formed for electrical insulation. The secondary protective layer 700 has contact holes for contact with the top contact.

After the inorganic LED device 300 is bonded to the flexible substrate 500 by the transferring element 600, and before the top electrode 800 is formed on the inorganic LED device 300, the secondary protective layer 700 may be an intermediate layer formed in an empty space around the inorganic LED device to separate the top electrode from the bottom electrode.

Figure 12:
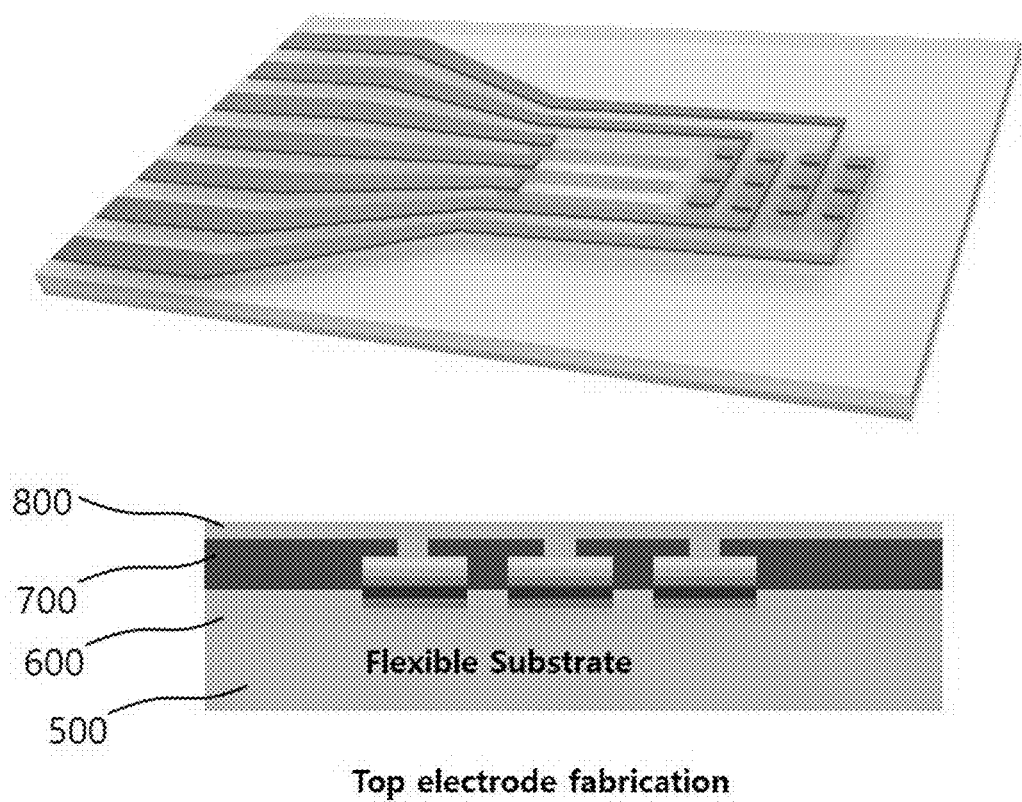

Referring to FIG. 12, the top electrode 800 is formed on the secondary protective layer 700.

In this instance, when quantum dots (QDs) as a color filter are applied to the cell of the LED, RGB pixel can be formed, and through this, flexible display can be realized.

Figure 13:
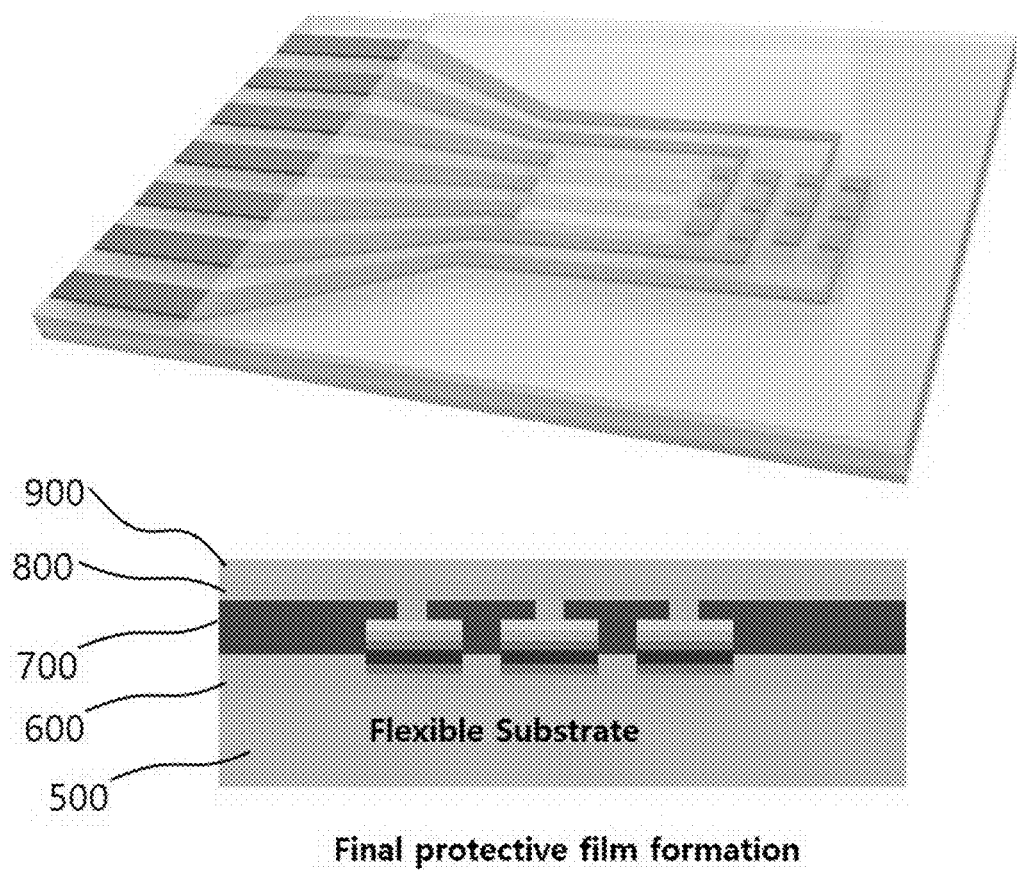

Referring to FIG. 13, a final protective film or passivation film 900 is formed, covering over the secondary protective layer 700 and the top electrode 800.

Figure 14:
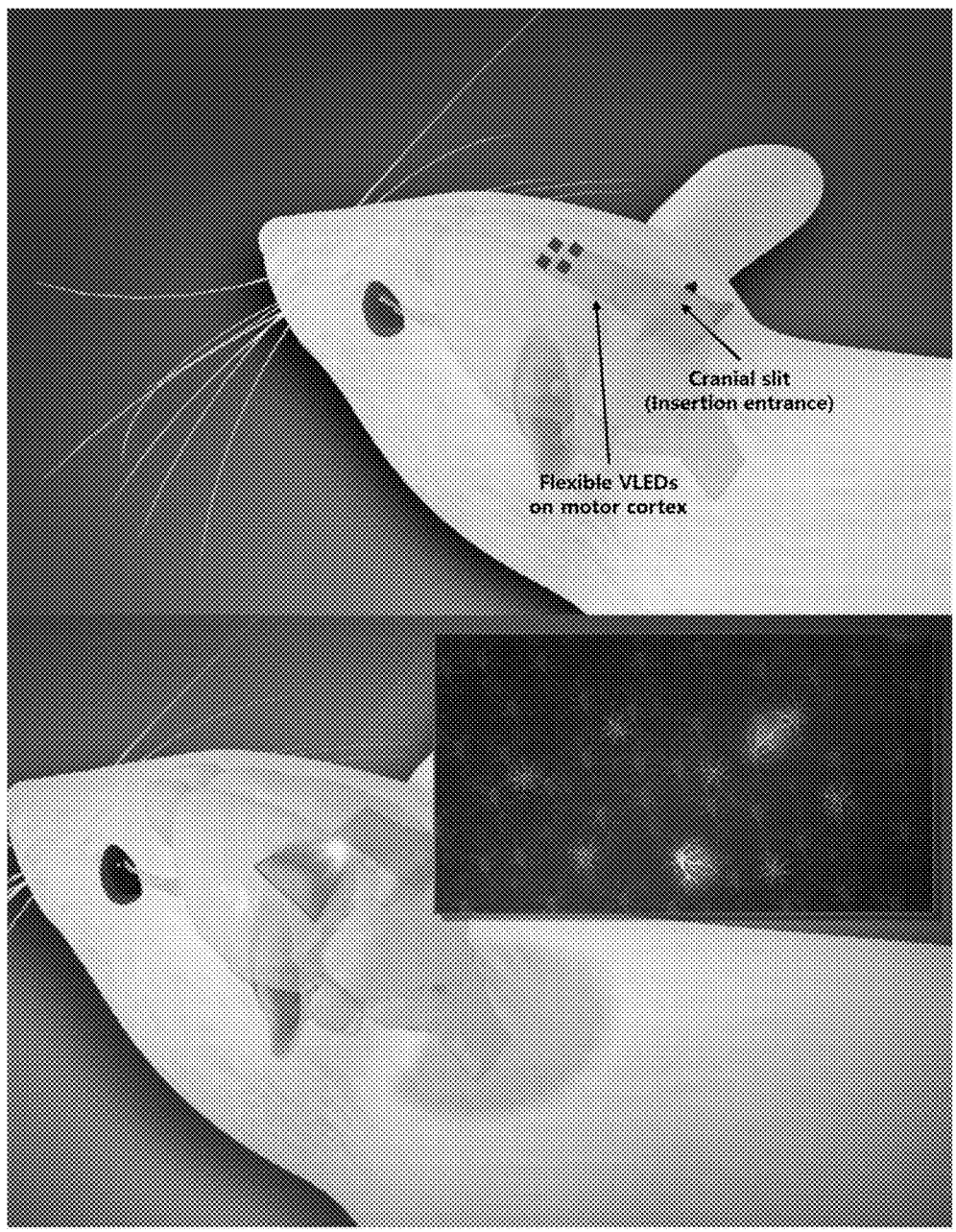
FIG. 14 is a feature that the micro inorganic LED device can be implanted into a narrow space between brain and skull of a rodent.

Referring to FIG. 14, an exemplary final structure of the micro inorganic LED device implanted into a narrow space between brain and skull of a rodent are shown.

The final structure of the flexible micro inorganic LED device is flexible vertical micro inorganic LEDs, and exhibits a structure in which interconnection is formed between two electrodes above and below the LED. This structure has a large window through which light is emitted, and thus it provides high light emission efficiency and is easy to integrate and effective in heat dissipation. Furthermore, it is suitable for flexible devices.

The micro inorganic LED is so thin and flexible that it can be implanted into a narrow space between brain and skull.

As shown in FIG. 14, the flexible micro LED fabricated by present disclosure can be used for optogenetics research and for the treatment of diseases using photogenetics.

It is not only possible to realize flexible display using the micro-sized inorganic LED, but also to use in the applications for inorganic LED lighting, wearable devices, and bio-integrated devices.

The present disclosure uses anisotropic conductive film (ACF) for transfer of the LED, which enables simultaneous transfer and interconnection, leading to a stable process, and accordingly, it allows mass production and is suitable for commercialization.

Figure 15:
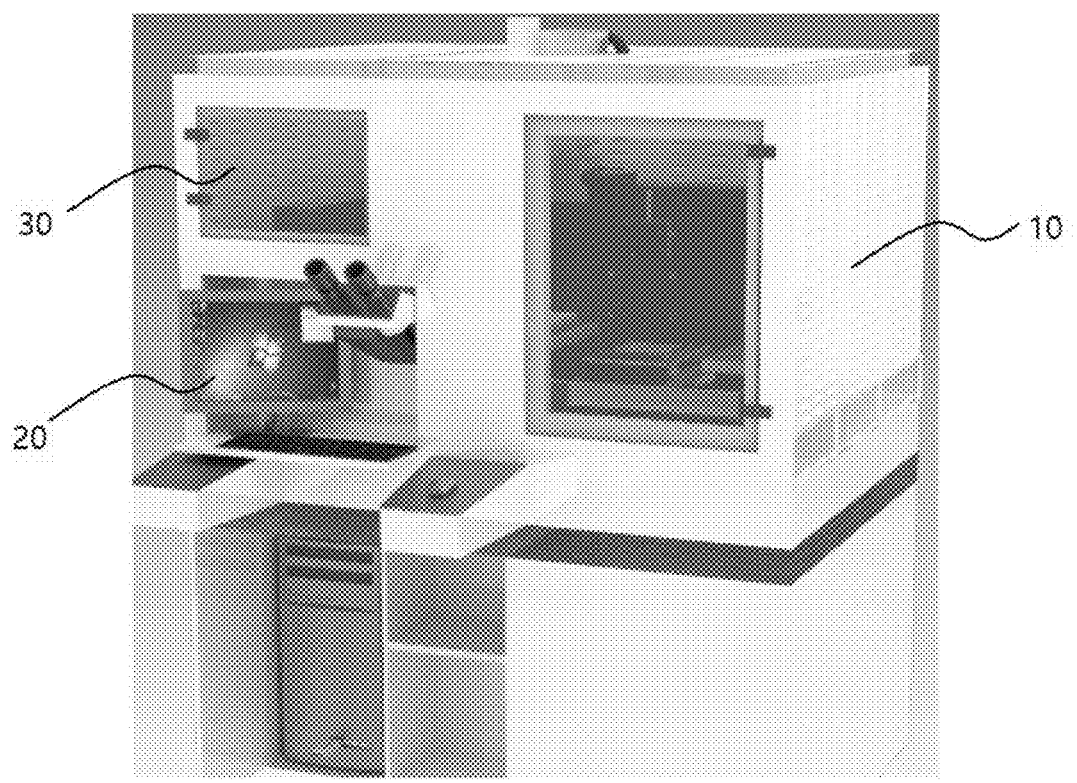
FIG. 15 shows an overall appearance of a transferring apparatus for fabricating a flexible electronic device according to an embodiment of the present disclosure.
Figure 16:
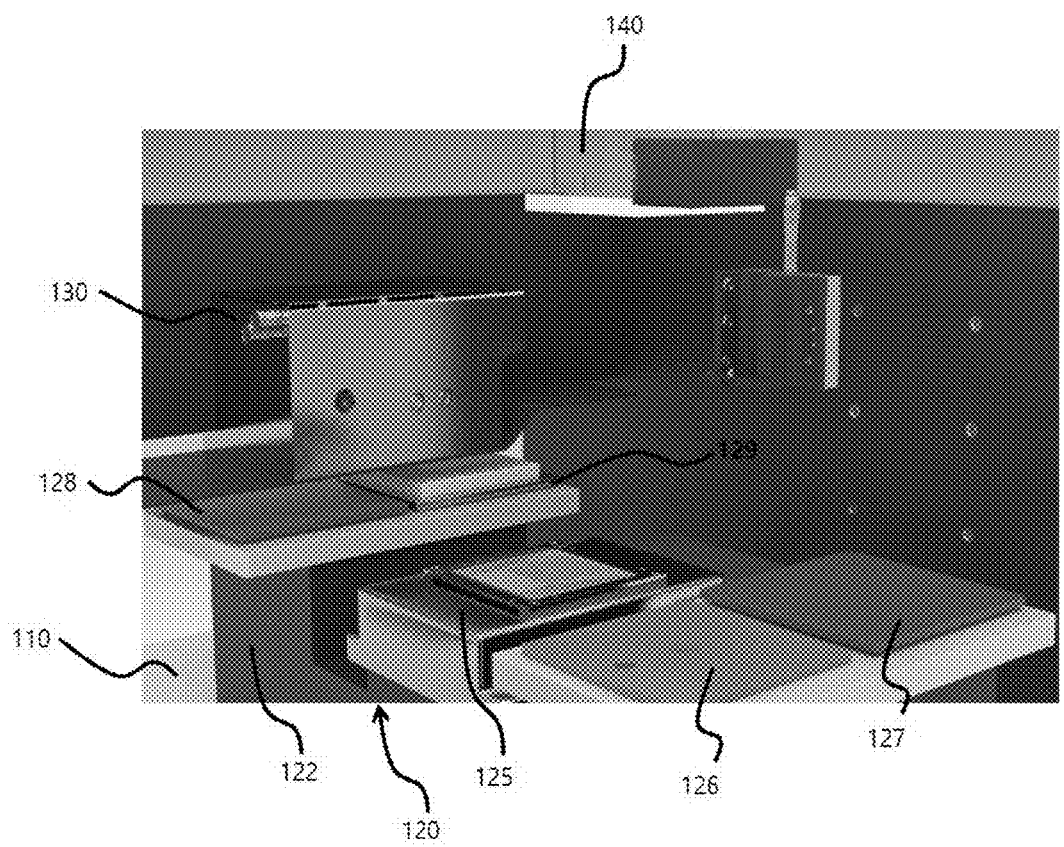
FIG. 16 shows the detailed configuration of the transferring apparatus according to FIG. 15.

Subsequently, a transfer and packaging apparatus for fabricating a flexible electronic device according to the present disclosure is described in detail with reference to FIGS. 15 to 17.

The transfer and packaging apparatus includes a hollow process chamber 1, a base plate 10 placed in the process chamber 1, a motion module (not shown) placed on the base plate 10, a stage module 20 placed moveably parallel to the ground by the motion module, an optical controller 30 placed moveably above the stage module 20 apart from the stage module 20, and a carrier substrate suction unit 40 placed above the stage module 20 such that it can be moved up and down.

The process chamber 1 may include a vacuum pump and a separate dust collector to create a clean space in which a transfer and packaging process is performed. The process chamber maintains a vacuum lower than the atmospheric pressure, thereby ensuring much higher yield and workability under a non-vacuum and obtaining high-quality products. The process chamber may be equipped with a transparent monitoring window through which the inner part can be observed or a display using an imaging device installed inside. In the transfer and packaging apparatus, the process chamber may be selectively employed, and the transfer apparatus may be manufactured without installing the process chamber.

The base plate 10 acts as a support of the transfer and packaging apparatus, and basically, may have a damper to provide high rigidity and prevent vibration and buffer impacts.

The XY axes as introduced herein define a direction of movement parallel to the ground, the X axis denotes a horizontal direction and the Y axis denotes a vertical direction. Meanwhile, Z axis defines a direction perpendicular to the ground, and is orthogonal to both the X axis and the Y axis.

The motion module moves the stage module along the directions of XY axes on the base plate, and includes an X axis motion unit and a Y axis motion unit which moves the stage module in the direction perpendicular to the X axis motion unit.

The carrier substrate suction unit can accurately move the electronic device by moving up and down above the stage module, and enables simultaneous transfer and interconnection by accurately adjusting the pressure and speed.

The pressure applied on the electronic device using the carrier substrate suction unit 40 is an important factor in transfer/interconnection using ACF and NOCF, and the speed of movement of the electronic device is an important factor to a stamping method. This is closely related to the possibility of transfer success changing depending on the speed of transfer of the carrier substrate.

The pressure and speed applied by the transfer and packaging apparatus is freely adjusted through the carrier substrate suction unit. That is, the pressure may be adjusted to the range of 1 kg-20 kg, and the speed may be adjusted to 1 μm/s-1000 mm/s.

The stage module 20 includes a stage support 22 placed on the motion module and multiple stages fixed on the stage support 22. The multiple stages include respective stages to enable transfer using various protocols including a stamping method, ACF, SOCF, and UV. That is, any one of the multiple stages placed along the XY plane is positioned to perform a transfer process through the movement of the stage support by the operation of the motion module.

For precise alignment, the stage module 20 can freely rotate the angle of the stage support 22 on the xy, yz, and zx planes.

As an embodiment, the multiple stages may be symmetrically arranged on two sides with respect to a first stage 25 at the center. Specifically, the multiple stages include second and third stages 26, 27 arranged side by side on one side of the first stage 25, and fourth and fifth stages 28, 29 arranged on the opposite side to the second and third stages 26, 27 with respect to the first stage 25.

The stage module 20 is replaced according to the purpose because stage deformation may occur when various transfer protocols are applied to a stage.

For example, heat and pressure may be simultaneously applied to the first stage 25, only the pressure may be applied to the second stage 26, and UV irradiation may be applied to the third stage 27.

Meanwhile, a stamping process may be performed through the fourth and fifth stages 28, 29.

Specifically, when the temporarily used transferring element is fixed on the carrier substrate suction unit 40 by suction and the stage module 20 is moved to place the mother wafer positioned on the fourth stage 28 below the carrier substrate suction unit 40, the LED inorganic multilayer on the mother wafer is positioned on the transferring element. Subsequently, the stage module 20 is appropriately moved and aligned so that the target substrate positioned on the fifth stage 29 is placed immediately below the carrier substrate suction unit 40. The alignment process can be performed through the optical controller placed between the fifth stage and the carrier substrate suction unit.

On the whole, the integrated electronic device or the LED inorganic multilayer on the mother wafer is transferred to the carrier substrate attached to a sample chuck constituting part of the carrier substrate suction unit. Subsequently, the integrated electronic device on the mother wafer is transferred onto the target substrate through a process for transferring the electronic device on the carrier substrate onto the target substrate.

The transfer and packaging apparatus according to the present disclosure enables a continuous 3D laminating process of the electronic device on the target substrate through the stage module, the optical controller and the carrier substrate suction unit. That is, it enables simultaneous interconnection and transfer of the electronic device of the carrier substrate held on the carrier substrate suction unit to the target substrate using the transferring element.

The optical controller 30 is placed between the carrier substrate suction unit and the stage module via a transfer process along the direction of X axis through a separate motion device. As a specific embodiment, when the first stage positioned at the center among the multiple stages is placed immediately below the carrier substrate suction unit, the optical controller is placed between the first stage and the carrier substrate suction unit.

The optical controller monitors the carrier substrate on the upper side and the target substrate simultaneously while moving between the carrier substrate held on the carrier substrate suction unit and the target substrate held on the first stage. For accurate alignment during this process, microscopic images are monitored through a computer connected to the apparatus. That is, the optical controller monitors the electronic device attached to the temporary carrier substrate on the upper side and the target substrate on the lower side simultaneously on one display, thereby achieving accurate alignment.

In this instance, images of the carrier substrate on the upper side and the target substrate on the lower side are displayed on the monitor in an overlapping manner, and a user directly aligns them by XY axes movement and angle adjustment. The optical controller functions as a special microscope to enable precise alignment. Here, misalignment is minimized through angle adjustment in xy, yz and zx directions for each stage to which the target substrate and the carrier substrate are fixed. Furthermore, it is possible to freely control the pressure and the movement speed of the stage along the directions of x, y and z axes, and enable process automation repeatedly through own programming.

The present disclosure enables transfer using various protocols including a stamping method, ACF, SOCF, and UV.

A process for transferring the electronic device on the carrier substrate onto the target substrate is as below.

The positions of the bottom electrode formed on the flexible substrate or the target substrate and the LED chip on the carrier substrate are aligned, and the transferring element is interposed between the target substrate and the carrier substrate. In this state, bonding is performed on the transferring element using any one of thermocompression techniques including ultrasonic wave, mechanical force, van der Waals force, and heat and pressure.

Meanwhile, the process for connecting the transferring element between the target substrate and the carrier substrate is not limited to a bonding process, and many different techniques or processes enabling connection or joint between multiple substrates may be applied.

Additionally, a heat wire is inserted into any one of the multiple stages to freely control the temperature of the target substrate and the carrier substrate, and through this, the range of applications of the transfer method is widened.

Meanwhile, the present disclosure may fabricate the electronic device using the transferring element by a roll-to-roll method.

Figure 17:
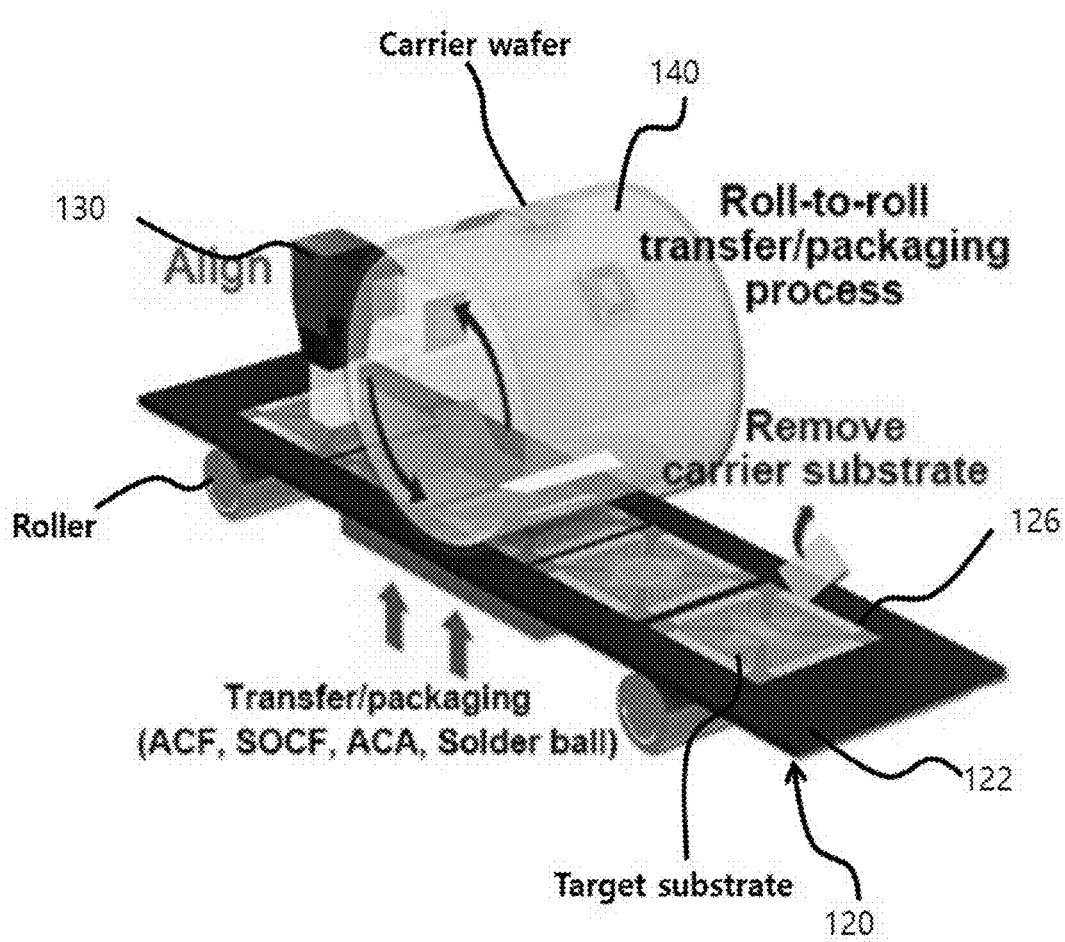
FIG. 17 shows a scheme for transferring an electronic device by a roll-to-roll method.

Seeing the roll-to-toll method, as shown in FIG. 17, the stage module 20 according to another embodiment includes a stage support 22 supported by multiple rollers and multiple stages fixed on the stage support 22. In FIG. 17, the carrier substrate is removed at one stage 26 of the multiple stages arranged in a line along the lengthwise direction of the stage support 22.

The carrier substrate suction unit is placed on the stage module in the shape of a roll that is attached along the circumference of multiple carrier substrates.

Here, the stage support is transferred by the multiple rollers. The target substrate that receives the electronic device from the carrier substrate is placed on the multiple stages of the stage support.

When the optical controller is placed on one side of the carrier substrate suction unit, the carrier substrate attached to the carrier substrate suction unit in a roll shape and the target substrate placed on the multiple stages are monitored simultaneously. That is, as an embodiment, the carrier substrate attached to the carrier substrate suction unit is monitored through the side of the optical controller, and at the same time, the target substrate is monitored through the bottom of the optical controller.

After position alignment is accomplished through the optical controller, a transfer and packaging process is performed by the pressure applied between the target substrate and the carrier substrate positioned at the bottom among the carrier substrates attached to the carrier substrate suction unit that works with rotation, and subsequently, the carrier substrate is removed, to complete the transfer of the LED chip on the carrier substrate onto the target substrate.

Meanwhile, the stage module may be formed in the shape of the same roll as the carrier substrate suction unit. Here, the carrier substrate suction unit and the stage module formed of multiple rollers are configured to face each other, but the distance between rollers facing each other differs. Particularly, as the distance between rollers becomes shorter, the distance between multiple stages also becomes shorter, and device transfer is accomplished by the multiple stages at the reduced distance.

In the present disclosure, multiple transferring elements are arranged at a predetermined interval in the circumferential direction along the circumference of the carrier substrate suction unit having a roll shape. The interval of arrangement is set to match the distance between multiple stages.

In the present disclosure, using the mother wafer serving as a fixed substrate which protects a sensitive flexible VLSI rather than the flexible VLSI device, the electronic device is bonded to the transferring element held by the carrier substrate suction unit, and then, the electronic device bonded to the transferring element is automatically bonded again to the flexible substrate or the target substrate in the direction below the transferring element, thereby achieving relatively stable device transfer.

As described above, the present disclosure forms the LED inorganic multilayer that makes up an inorganic LED on the mother wafer, enables isolation of each chip through etching, transfers the isolated LED chips onto the flexible substrate with electrodes by the medium of anisotropic conductive film and enables interconnection, thereby realizing the flexible LED device in the form of an individual chip or an array, and the anisotropic conductive film (ACF) is used in the process for transfer the LED, thereby providing an adhesive strength for transfer and enabling electrical interconnection, leading to a simple and stable process.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A method for fabricating an electronic device using a transferring element comprising:
    preparing a mother wafer;
    forming an inorganic material-based multilayer thin film layer which makes up an electronic device on the mother wafer;
    individually isolating the electronic device formed on the multilayer thin film layer;
    attaching a carrier substrate to the electronic device;
    removing the mother wafer;
    aligning positions of a bottom electrode formed on a target substrate and the electronic device on the carrier substrate;
    placing a transferring element between the target substrate and the electronic device, and performing transfer and interconnection;
    removing the carrier substrate; and
    forming a top electrode connected to the electronic device after the removing of the carrier substrate.

2. The method for fabricating an electronic device using a transferring element of claim 1, wherein the target substrate is a flexible plastic substrate or a polymer substrate.

3. The method for fabricating an electronic device using a transferring element of claim 1,
    wherein the attaching of the carrier substrate to the electronic device formed on the multilayer thin film comprises forming a primary protective layer on a side surface of the electronic device to protect the electronic device,
    wherein the primary protective layer is an oxide layer or a polymer layer.

4. The method for fabricating an electronic device using a transferring element of claim 3 further comprising:
    forming a secondary protective layer on an empty space around the electronic device to prevent a short between the bottom electrode and the top electrode before the forming of the top electrode,
    wherein the secondary protective layer is an oxide layer or a polymer layer.

5. The method for fabricating an electronic device using a transferring element of claim 1, wherein the electronic device is a large scale integrated circuit (LSI).

6. The method for fabricating an electronic device using a transferring element of claim 1, wherein the carrier substrate is any one of a group including PDMS, a thermal release tape, a UV release tape, and a water soluble tape.

7. The method for fabricating an electronic device using a transferring element of claim 1, wherein at the transfer and interconnection,
    when the transferring element is selectively applied to the target substrate and the electronic device temporarily attached to the carrier substrate is bonded, bonding is only performed on the electronic device placed on an area of the target substrate to which the transferring element is applied.

8. The method for fabricating an electronic device using a transferring element of claim 1, wherein at the transfer and interconnection,
    when only part of the electronic device on the carrier substrate is applied to the transferring element, the part of the electronic device is selectively transferred.

9. The method for fabricating an electronic device using a transferring element of claim 1, wherein at the transfer and interconnection,
    when the transferring element is entirely applied to the target substrate and the entire electronic device on the carrier substrate is bonded, simultaneous transfer and interconnection of the entire electronic device is achieved.

10. The method for fabricating an electronic device using a transferring element of claim 1, wherein the removing of the mother wafer is performed through etching or laser lift off process.

11. The method for fabricating an electronic device using a transferring element of claim 1,
    wherein the transferring element is any one of a group including anisotropic conductive film, Non Conductive Film (NCF), Self Organized Conductive Film (SOCF), Anisotropic Conductive Adhesive (ACA) and solder ball, wherein the transfer and interconnection uses any one of bonding means including ultrasonic wave, mechanical force, van der Waals force, and heat and pressure.

12. The method for fabricating an electronic device using a transferring element of claim 1,
wherein the individually isolating of the electronic device comprises isolating the electronic device for each chip through masking and etching,
wherein the masking is any one of a group including metal masking, masking using PR, masking using polymer, and soft masking.

* * * * *